US008794859B1

(12) United States Patent
Patterson

(10) Patent No.: US 8,794,859 B1
(45) Date of Patent: Aug. 5, 2014

(54) APPARATUS, SYSTEM AND METHOD FOR DOVETAIL LOCKING MECHANISMS

(75) Inventor: Todd Ray Patterson, Lockwood, MO (US)

(73) Assignee: Grand Rock, LLC, Tulsa, OK (US)

( * ) Notice: Subject to any disclaimer, the term of this patent is extended or adjusted under 35 U.S.C. 154(b) by 0 days.

(21) Appl. No.: 13/604,284

(22) Filed: Sep. 5, 2012

Related U.S. Application Data

(60) Provisional application No. 61/531,262, filed on Sep. 6, 2011.

(51) Int. Cl.
*B60P 1/44* (2006.01)
(52) U.S. Cl.
USPC .......................................... 403/102; 414/537
(58) Field of Classification Search
USPC ........................ 403/84, 85; 414/469, 480, 537
See application file for complete search history.

(56) References Cited

U.S. PATENT DOCUMENTS 5,215,426 A * 6/1993 Bills, Jr. ......................... 414/537
6,394,734 B1 * 5/2002 Landoll et al. ................. 414/480

\* cited by examiner

*Primary Examiner* — Michael P Ferguson
*Assistant Examiner* — Daniel Wiley
(74) *Attorney, Agent, or Firm* — Frederic Dorwart, Lawyers; Penina Michlin Chiu

(57) ABSTRACT

Apparatus, systems and methods for dovetail locking mechanisms are described herein. A system for locking the dovetail of a trailer in the travel position includes a sled for locking the dovetail of a trailer in the travel position, a railing on the underside of the trailer to accommodate the sled, wherein the sled is moveably attached to the railing such that the sled can slide into a loading position clear of the dovetail or a travel position at least partially beneath the dovetail, and means for actuating the sled to the loading position and travel position. A method for locking the dovetail of a trailer includes moving the dovetail of a trailer into the travel position and sliding a sled from a loading position underneath the trailer to a travel position at least partially underneath the dovetail of the trailer.

11 Claims, 4 Drawing Sheets

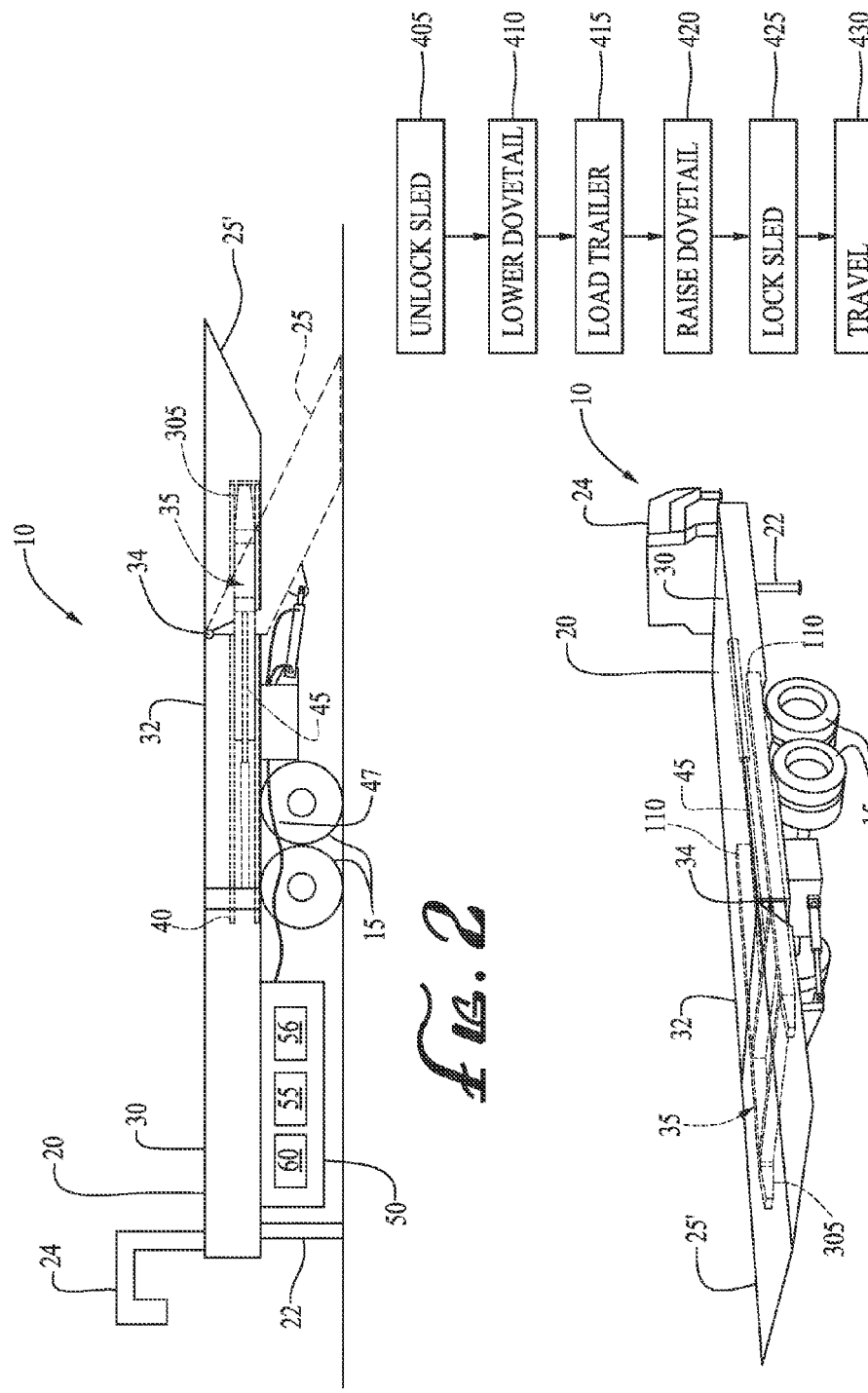

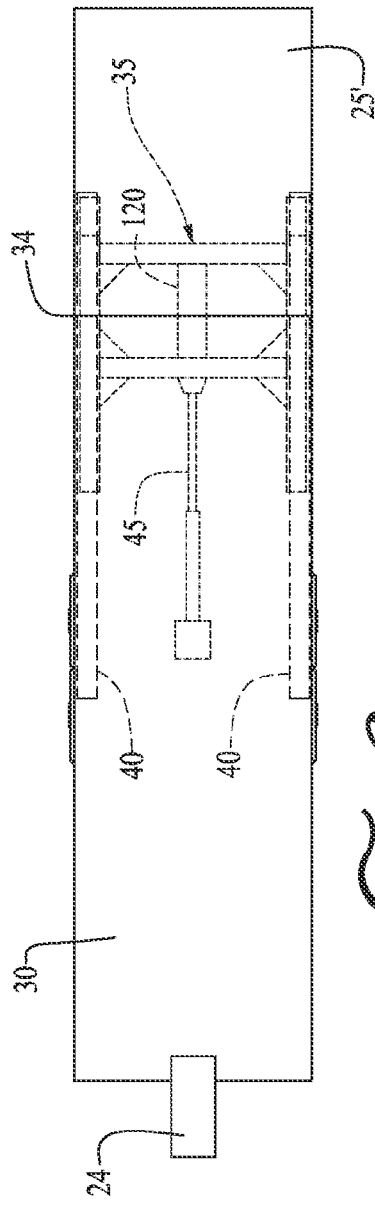
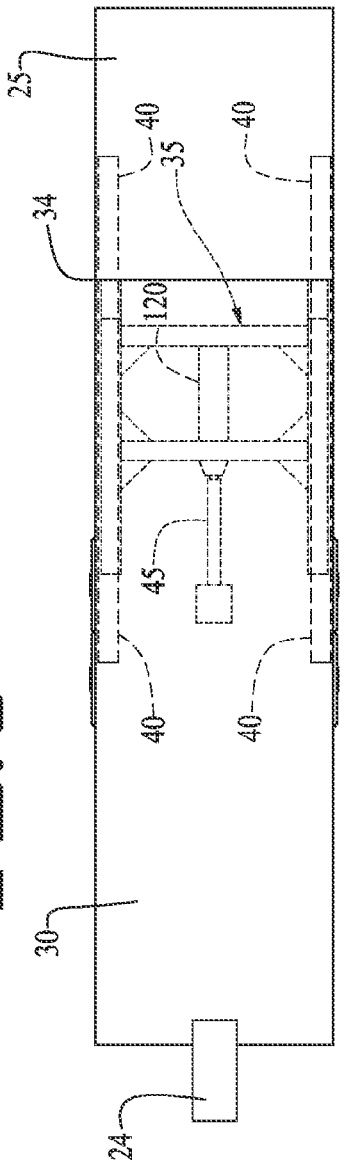

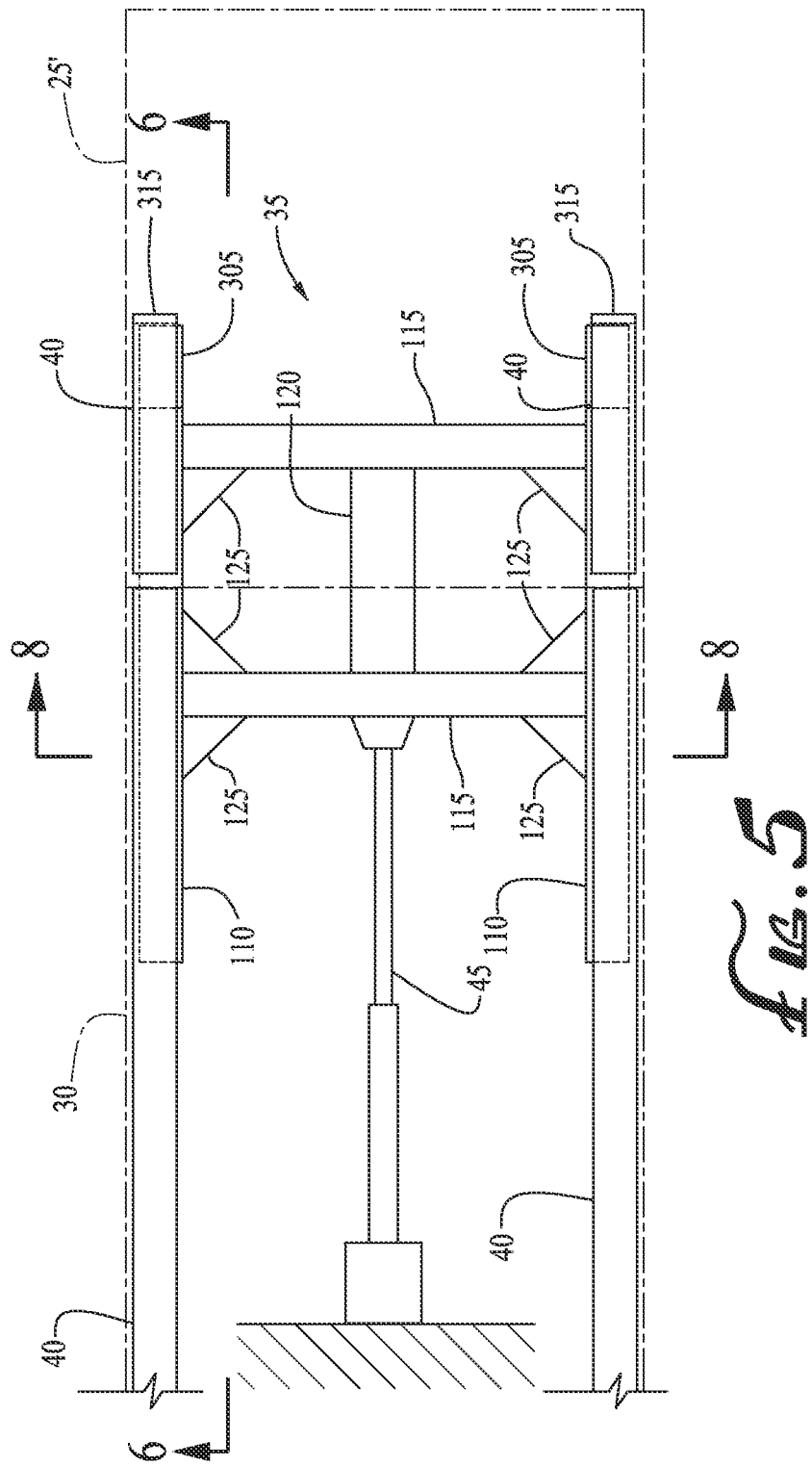

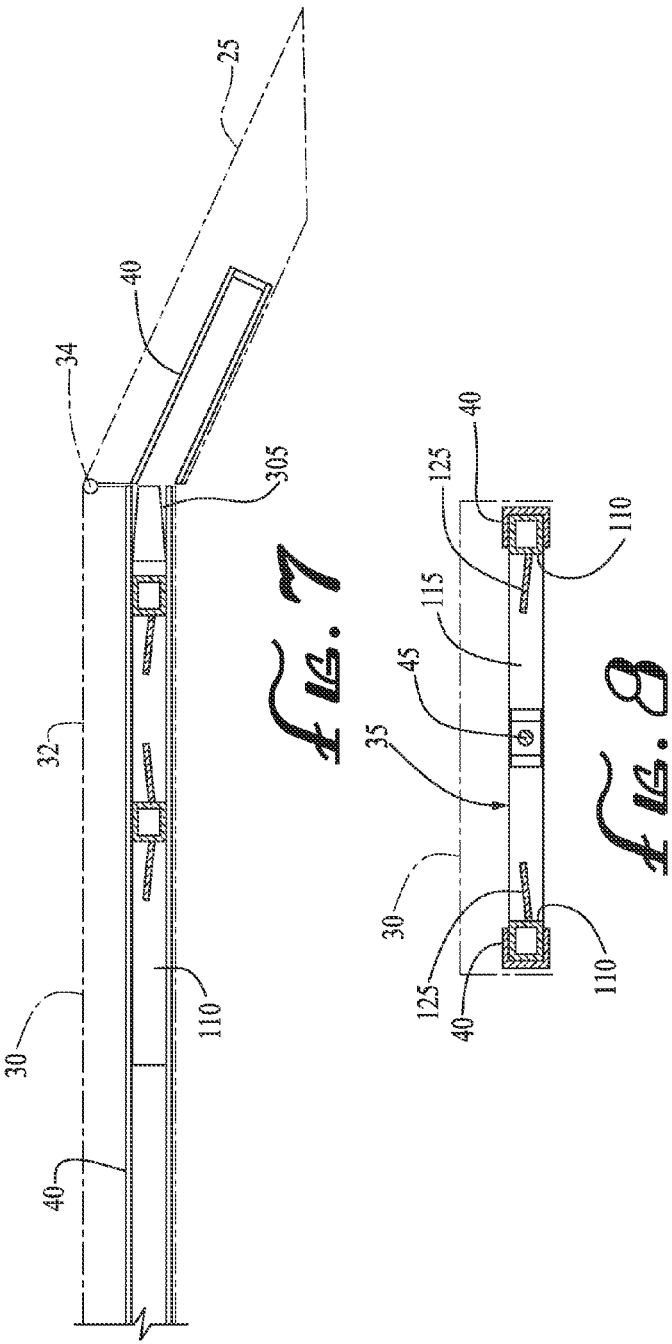

APPARATUS, SYSTEM AND METHOD FOR DOVETAIL LOCKING MECHANISMS

CROSS REFERENCE TO RELATED APPLICATIONS

This application claims the benefit of U.S. Provisional Application No. 61/531,262 to Patterson, filed Sep. 6, 2011 and entitled "Apparatus, System and Method for Dovetail Locking Mechanisms," which is hereby incorporated by reference in its entirety.

BACKGROUND OF THE INVENTION

1. Field of the Invention

Embodiments of the invention described herein pertain to the field of vehicle trailers. More particularly, but not by way of limitation, one or more embodiments of the invention enable an apparatus, system and method for dovetail trailer locking mechanisms.

2. Description of the Related Art

Flatbed trailers are often used to transport heavy or large materials such as farming equipment, goods and materials such as tractors, fencing and corral material, livestock equipment or hay and feeding equipment. Such trailers may also be used to transport automobiles, construction equipment and other large and/or heavy items that would benefit from loading and unloading on a flatbed truck using a ramp. Therefore, some flatbed trailers include a "dovetail"—a portion of the flatbed that can be lowered to the ground in order to create a ramp at the end of the trailer. In this way, equipment, goods and materials can be loaded onto and unloaded from the flatbed trailer more easily. Some dovetail-type flatbed trailers require that the ramp be lowered and raised mechanically. Other flatbed trailers have dovetails that may be raised and lowered hydraulically.

Traditionally, when the dovetail is in the raised position it is held in place using steel pins. Use of pins requires slack in the receiving hole. The slack causes solid shaking when the trailer is travelling, which reduces stability of the trailer. In addition, the dovetail portion of a trailer, when secured by pins, can only accommodate a limited amount of weight. This limits the size and placement of the load the trailer is able to carry and negatively affects weight distribution on the trailer. Limitations of conventional dovetail trailers may also negatively affect towing safety.

Traditional flatbed trailers may also be susceptible to damage due to human error. If the dovetail is accidentally lowered while the pins are still in place, this may cause extensive damage to the trailer that is costly to repair. Furthermore, when a conventional dovetail trailer is rear-ended by another vehicle, the dovetail may flip upwards, with the colliding vehicle sliding underneath the trailer causing serious damage and injury. Finally if the hydraulics that operate the dovetail malfunction, the pins alone cannot hold the weight of the dovetail or any load placed on the top of it. In such an instance, a conventional dovetail trailer may collapse.

Conventionally, dovetail trailers may use C-shaped brackets instead of pins to hold the dovetail in the raised position. These C-shaped brackets suffer from many of the same drawbacks as the pins.

For at least the limitations described above, there is a need for an apparatus, system and method for dovetail locking mechanisms.

BRIEF SUMMARY OF THE INVENTION

One or more embodiments of the invention enable an apparatus, system and method for flatbed trailer dovetail locking mechanisms. In some embodiments, a system for locking the dovetail of a trailer in the travel position includes a sled for locking the dovetail of a trailer in the travel position, a railing on the underside of the trailer to accommodate the sled, wherein the railing extends underneath the dovetail of the trailer and wherein the sled is moveably attached to the railing such that the sled can slide into a loading position clear of the dovetail or a travel position at least partially beneath the dovetail, a gap in the railing to allow the dovetail to be actuated into a loading position or a travel position, and means for actuating the sled to the loading position and travel position. In some embodiments, the sled is made of steel or alloy steel. In certain embodiments the ram is a hydraulic ram. In further embodiments, the ram at least partially holds the sled in place. In some embodiments, the sled includes two tubes parallel to the railing and a connecting tube that connects the parallel tubes to one another.

A method for locking the dovetail of a trailer includes moving the dovetail of a trailer into the travel position and sliding a sled from a loading position underneath the trailer and clear of the dovetail of the trailer to a travel position at least partially underneath the dovetail of the trailer. In some embodiments the sled slides along a railing on the underside of the trailer and the railing extends at least partially underneath the dovetail of the trailer.

BRIEF DESCRIPTION OF THE DRAWINGS

The above and other aspects, features and advantages of the invention will be more apparent from the following more particular description thereof, presented in conjunction with the following drawings wherein:

FIG. 1 is a perspective view of a flatbed trailer comprising one or more embodiments of a dovetail locking mechanism.

FIG. 2 is a side view of a flatbed trailer comprising one or more embodiments of a dovetail locking mechanism FIG. 3 is a plan view of one or more embodiments of a flatbed trailer comprising a dovetail locking mechanism in travel position.

FIG. 4 is a plan view of a flatbed trailer comprising one or more embodiments of a dovetail locking mechanism in loading position.

FIG. 5 is a plan view of one or more embodiments of a sled and railings.

FIG. 6 is cross section view taken along line 6-6 of FIG. 5 of one or more embodiments of a sled in travel position.

FIG. 7 is a cross section view taken along line 6-6 of FIG. 5 of one or more embodiments of a sled in loading position FIG. 8 is a cross section view taken along line 8-8 of FIG. 5 of one or more embodiments of a sled and railings.

FIG. 9 is a flowchart showing a method to secure the dovetail of a flatbed trailer for travel.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

An apparatus, system and method for dovetail locking mechanisms will now be described. In the following exemplary description numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

As used herein, "coupled" refers to either a direct connection or an indirect connection (e.g., at least one intervening connection) between one or more objects or components.

As used herein, "lock" or "locked" refers to the sled and/or the dovetail when in or placed in the travel position and "unlock" or "unlocked" refers to the sled and/or the dovetail when in or placed in the loading position.

As used herein, "actuate" refers to the moving or changing the position of a dovetail and/or sled relative to the flatbed trailer—either moving it into the travel position or the loading position.

As used in this specification and claims, the singular forms "a", "an" and "the" include plural referents unless the context clearly dictates otherwise. Thus, for example, reference to a railing includes one or more railings.

Using the apparatus, systems and methods described herein, the dovetail portion of a flatbed trailer may be secured in the travel position without the need for conventional pins or C-brackets. In some embodiments, the dovetail may be secured using a sled. In certain embodiments, the sled may be hydraulically actuated. In some embodiments, any hinged portion of a trailer may be secured and capable of supporting heavy loads through the use of a sled. In certain embodiments, the sled may be actuated to the locked or unlocked position using one or more hydraulic rams and may slide along a railing on the underside of the trailer.

The apparatus, systems and methods described herein, prevent unwanted bending and shaking of a dovetail when the dovetail is in the travel (raised) position. Undesirable bending or shaking may occur in a trailer comprising a dovetail due to a heavy load, a collision, rough terrain or the weight of the dovetail itself against its pins or support brackets. In addition, the apparatus, systems and methods described herein allow a dovetail with the described locking mechanism to support significantly heavier cargoes than conventional dovetails. The dovetail of the invention typically may support loads of up to 15,000 pounds on the dovetail and lift up to about 10,000 pounds on the dovetail, depending on the specific characteristics and size of the trailer and sled. In comparison, a comparable conventional dovetail may only support loads of up to about 10,000 pounds on the dovetail and lift up to about 7,500 pounds on the dovetail. Furthermore, the apparatus, systems and methods described herein limit damage to the trailer due to human error by preventing movement of the dovetail when an operator attempts to actuate the dovetail while the sled is still in the locked position.

FIG. 1 depicts a perspective view of a flatbed trailer comprising one or more embodiments of a dovetail locking mechanism. Trailer 10 may include wheels 15 and front end 20. Front end 20 may include gooseneck 24 and/or may be attached to a truck, semi or cab (not shown). In some embodiments, leg(s) 22 assist in supporting trailer 10 while trailer 10 is stationary or being loaded or unloaded. Leg(s) 22 may be raised and lowered mechanically, pneumatically or hydraulically. Leg(s) 22 may be controlled by remote control or a control pad located on trailer 10. The number of and location of wheels 15 will vary based on the size of trailer 10. For example, trailer 10 may include two wheels, six wheels, eight wheels, or twelve or more wheels, or any number of wheels appropriate for the size and type of trailer 10.

Trailer 10 may include flatbed 30 and dovetail 25'. Dovetail 25' may be a portion of flatbed 30 and/or trailer 10 that is capable of being lowered for loading of trailer 10. In FIG. 2, dovetail 25' is shown at rear end 32 of flatbed 30 and depicted in alternative lowered position 25 for loading. Dovetail 25 may be made of steel, wood, any combination of the two or any other suitable materials and located at any end of flatbed 30, such as rear end 32. Dovetail 25 may be eight, nine or ten feet in length, but shorter or longer lengths are also contemplated depending on the size of trailer 10 and the purpose and location of dovetail 25. In some embodiments, dovetail 25 may be on any side of flatbed 30. Dovetail 25 may be actuated into raised position 25' for traveling so that it is substantially even with flatbed 30. Dovetail 25 may be raised and lowered using mechanical, hydraulic or pneumatic systems well known to those of skill in the art. In some embodiments, dovetail 25 may be raised or lowered hydraulically and one or more hydraulic rams, cylinders, pistons, hoses and valves may be located on the underside of trailer 10 for such purpose. In certain embodiments, dovetail 25 rotates on hinge 34. Hinge 34 may be any type of suitable hinge, such as a piano hinge, continuous hinge, butt hinge, pivot hinge, barrel hinge, or any other type of bearing capable of connecting two solid objects and allowing an angle of rotation between them. In other embodiments, hinge 34 may be any type of pivot or rotational element that allows dovetail 25 to move in one or more directions.

In certain embodiments, sled 35 is moveably attached to the underside of flatbed 30. In some embodiments, sled 35 is made of steel or alloy steel, such as steel tubes, piping or bars, and fitted into railings 40 (shown in FIG. 2) on the underside of flatbed 30, such that it may slide into the travel position towards dovetail 25' to lock, or into the loading position away from dovetail 25' (towards front end 20) to unlock. When in the travel position, sled 35 may at least partially extend underneath dovetail 25'. When in the loading position, sled 35 may be clear of dovetail 25, 25' so as to allow dovetail 25' to move into the loading position. The size of sled 35 will depend on the size of flatbed 30 and dovetail 25. In certain embodiments, sled 35 may be eight feet in length of which up to four feet of length may sit below dovetail 25' when sled 35 in the travel position. Other sizes and lengths of sled 35 are also contemplated. In some embodiments, sled 35 is substantially the same width as flatbed 30. In other embodiments, sled 35 is narrower or wider than flatbed 30.

As shown in FIG. 3, sled 35 may be actuated (moved) to the travel position to allow dovetail 25' to be secured into travel position 25'. As shown in FIG. 4, sled 35 may be actuated to the loading position to allow dovetail 25' to move into loading position 25. Actuation may be hydraulic, mechanical or pneumatic. Movement in other directions is also contemplated depending on the relative location of dovetail 25, 25' and sled 35. In some embodiments, one or more hydraulic rams 45, which include a piston and cylinder, engage and release sled 35. In certain embodiments, hydraulic cylinder of ram 45 is fully extended when sled 35 is in the travel position. Hoses 47, shown in FIG. 2, may couple hydraulic ram 45 to pump 55, motor 56, and hydraulic fluid reservoir (not shown) located inside tool box 50. Tool box 50 may also house one or more batteries and/or remote control 60 for remotely operating hydraulic ram 45 thereby remotely engaging or releasing sled 35. In certain embodiments, sled 35 may be powered by rechargeable batteries, the battery of the truck that is coupled to trailer 10, lithium batteries, solar powered batteries or any other type of powering system well known to those of skill in the art. Remote control 60 may be wired or wireless and contain buttons or levers for an operator to control hydraulic ram 45 and/or sled 35. Remote control 60 may also control operation of dovetail 25.

Valves, switches, pistons, cylinders, pressure regulators, wiring and fittings well known to those of skill in the art may also be used with hydraulic ram 45 in connection with actuating (engaging or releasing) sled 35 and located on trailer 10, for example on the underside of trailer 10, on the side of trailer 10 or in tool box 50. Hydraulic ram 45 may be secured with a brace, such as a U-shaped brace, to prevent movement in undesirable directions, prevent shaking during movement or travel and/or to secure hydraulic ram 45 to the underside of trailer 10 and/or otherwise attach hydraulic ram 45 to trailer 10. Hoses 47 may be surrounded by protective casing.

FIG. 5 illustrates a plan view of one or more embodiments of sled 35 as seen from below. Parallel tubes 110 fit into one or more railings 40 located on the side or underside of trailer 10, on the underside of flatbed 30 and/or on the underside of dovetail 25. In some embodiments, parallel tubes 110 are parallel or substantially parallel to railings 40 and the length of trailer 10, such that one or more parallel tubes 110 may move along railings 40 thereby sliding sled 35 into the travel or loading position. As shown in FIGS. 3-5, railings 40 may be located near the periphery of the underside of flatbed 30 and dovetail 25. In some embodiments, one or more railings 40 may be located in any location between the outer edges of trailer 10 on the underside of trailer 10, flatbed 30 and/or dovetail 25. Parallel tubes 110 may be hollow or solid and comprised of rectangular, square, circular, oval or other shaped tubing. Lubricant may be applied to railings 40 to assist in the sliding motion of sled 35 and/or parallel tubes 110 along railings 40.

As shown in FIG. 5, in some embodiments, connecting tubes 115 may be coupled to parallel tubes 110 and contribute to stability of sled 35 when force is exerted onto sled 35 during actuation. In certain embodiments, connecting tubes 115 are perpendicular or substantially perpendicular to parallel tubes 110 and/or railings 40. In certain embodiments, connecting tubes 115 connect a first parallel tube 110 to a second parallel tube 110. In some embodiments, connecting tubes 115 are set at some angle to parallel tubes 110 that provides the necessary or desired stability to sled 35. In some common embodiments, parallel tubes 110 and/or sled 35 may be about eight feet in length, wherein a first connecting tube 115 may then be located about 38 inches along parallel tubes 110, as measured from the end of parallel tube 110 facing substantially towards front end 20, and a second connecting tube 115 may be located about 16 inches along parallel tubes 110 as measured from the end of parallel tube 100 facing substantially towards dovetail 25'. In some embodiments, connecting tubes 115 and/or parallel tubes 110 may be comprised of about four inch by six inch rectangular tubing.

In some embodiments, pipe 120 may be coupled to connecting tubes 115 to lend additional strength and durability to sled 35. In some embodiments, pipe 120 may be substantially parallel to parallel tubes 110 and railings 40. In some embodiments, where sled 35 and/or parallel tubes 110 are about eight feet in length, pipe 120 may be about 34 inches in length with an outer diameter of about four and a half inches. Pipe 120 may be hollow or solid, round, square, oval, rectangular or any other shape sufficient to provide the desired strength and durability.

Parallel tubes 110, connecting tubes 115 and pipe 120 may be made of steel or any other metal, composite or material capable of withstanding the durability and strength requirements of sled 35. Plate gussets 125 may be coupled to parallel tubes 110 and connecting tubes 115. In some embodiments, plate gussets 125 are a quarter inch thick. In some embodiments, one or more hydraulic ram 45, which may include a piston and cylinder, may be coupled to one or more connecting tubes 115 and slide sled 35 in the travel (locked) position or loading (unlocked) position.

FIGS. 6 and 7 are cross sectional views taken along line 6-6 of FIG. 5 of one or more embodiments of a sled. As shown in FIGS. 6 and 7, one or more ends of parallel tubes 110 may be tapered to assist parallel tubes 110 in movement along railings 40, across gap 310 or actuating sled 35 into place in the travel or loading position. Hydraulic ram 45 (shown in FIG. 5) may assist in holding or fully holding sled 35 in place while it is in the travel position (extended towards dovetail 25'). In some embodiments, the weight of dovetail 25' and any cargo on trailer 10, flatbed 30 and/or dovetail 25' also may assist in wedging sled 35 into position so it does not move during travel. In certain embodiments, the weight of dovetail 25' and any load on trailer 10 may be sufficient to hold sled 35 in place, even if hydraulic pressure is lost in hydraulic ram 45. In certain embodiments, sled 35 will not break and will hold dovetail 25' stationary in the instance that motion of dovetail 25' is inadvertently activated while sled 35 is still in the travel position.

FIG. 7 illustrates one embodiment of sled 35 coupled to railings 40 on the underside of flatbed 30 and dovetail 25. In FIG. 7, dovetail 25 is shown in the loading position illustrated as position 25. Parallel tube 110 may be fitted into railings 40 so as to attach sled 35 to the underside of flatbed 30 and/or dovetail 25, depending on whether sled 35 is in the locked (travel) or unlocked (loading) position. In some embodiments, parallel tubes 110 have tapered end 305 to assist in connecting tapered end 305 to railings 40 on the underside of dovetail 25 or flatbed 30. Stopper 315 may assist in keeping parallel tubes 110 in place and stopping the motion of parallel tubes 110 along railing 40. In some embodiments, gap 310 in railings 40 may allow dovetail 25 to actuate when sled 35 is in the loading position. When sled 35 is in the travel position, sled 35 fills gap 310 thereby preventing movement of dovetail 25', as shown in FIG. 6.

As shown in FIGS. 3 and 6, in certain embodiments, sled 35 will be at least partially below flatbed 30 and at least partially below dovetail 25' when in the travel (locked) position. As shown in FIGS. 4 and 7, in certain embodiments, sled 35 will be clear of dovetail 25 when in the loading position. In some embodiments, sled 35 will be clear of gap 310 when in the loading position such that dovetail 25 is free to move and bend and/or unbend at hinge 34.

FIG. 8 is a cross section view taken along line 8-8 of FIG. 5 of one or more embodiments of a sled and railings and further illustrates sled 35 and railings 40.

FIG. 9 illustrates a flowchart of an embodiment of a method to secure the dovetail of a trailer. If sled 35 is in the travel position, in step 405, sled 35 may be unlocked using hydraulic ram 45 into a loading position by sliding sled 35 along railings 40 away from rear end 32 and out from underneath dovetail 25' and/or gap 310, such that hinges 34 may be free to move. If sled 35 is initially in the loading position, step 405 may be unnecessary. At step 410, rear end of dovetail 25' may manually, hydraulically or pneumatically be lowered to the ground to create a ramp for loading trailer 10, as shown in FIG. 2. In some embodiments, trailer 10 may be loaded at step 415, for example by placing a trailer, farming and/or livestock equipment onto trailer 10. Equipment may be loaded onto either or both of flatbed 30 and dovetail 25.

When the operator is ready to travel or done loading trailer 10, dovetail 25 may be moved into a raised position at step 420, as shown in FIG. 2 in alternative position 25'. When in the raised position, dovetail 25' may form one long platform with flatbed 30. At step 425, sled 35 is moved into the travel (locked) position by actuating sled 35 along railings 40, such that parallel tubes 110 proceed past gap 310 (shown in FIG. 6) and into railings 40 on dovetail 25'. In some embodiments, parallel tubes 110 may proceed to a position where one quarter, one half, or three quarters of their length are along railings 40 located on dovetail 25. In other embodiments, parallel tubes 110 may proceed to any other position underneath dovetail 25 and flatbed 30 such that the weight of dovetail 25' and any load on either of them are supported. In some embodiments, at travel step 430, trailer 10 is ready for travel once sled 35 is in the travel (locked) position. If leg(s) 22 have been lowered during loading, they may be raised prior to travel.

As would be well understood by those of ordinary skill in the art, trailer 10 may also be unloaded using steps similar and/or the reverse of those described elsewhere herein.

The inventions described herein increase the stability and strength of conventional dovetail trailers. The sled of the invention reduces shaking of flatbed trailers when travelling since slack from pins is eliminated. The inventions described herein also increase the weight that the dovetail portion of a flatbed trailer is able to support. Damage to flatbed trailers due to human error or in collisions is also significantly reduced through the use of the inventions described herein, as the sled will not allow the dovetail portion of a flatbed trailer to move while the sled is in the travel position.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. In addition, it is to be understood that features described herein independently may, in certain embodiments, be combined.

What is claimed is:

1. A system for locking a dovetail of a trailer with respect to a flatbed of the trailer, the system comprising:
   a flatbed, the flatbed comprising a first railing formed on a periphery of an underside of the flatbed and extending to an end of the flatbed;
   a dovetail pivotally connected to the end of the flatbed at a pivot point, the dovetail comprising a second railing formed on a periphery of an underside of the dovetail, wherein the dovetail is pivotable between:
   a travel position, wherein the first railing and second railing are substantially aligned, and a gap is formed between the end of the flatbed and the end of the dovetail below the pivot point; and
   a loading position, wherein the dovetail is pivoted downward about the pivot point, such that the gap is closed; and
   a sled, the sled being slideably connected to the flatbed, and moveable via an actuating means attached to the flatbed, the sled comprising an elongate sliding member slideably engaged within the first railing, wherein the actuating means moves the sled between:
   a locked position, wherein when the dovetail is in the travel position, the sliding member is moved toward the dovetail so as to fill the gap and engage both the first and second railings, thereby preventing the dovetail from pivoting relative to the flatbed; and
   an unlocked position, wherein the sliding member is moved away from the dovetail so as to clear the gap, thereby allowing the dovetail to pivot relative to the flatbed into the loading position.

2. The system of claim 1, wherein the means for actuating the sled is a hydraulic ram.

3. The system of claim 1, wherein the sliding member has a tapered end.

4. The system of claim 1, wherein the sliding member is a tube.

5. The system of claim 4, wherein the tube is steel.

6. The system of claim 4, wherein the tube is rectangular.

7. The system of claim 4, wherein the tube is square.

8. The system of claim 4, wherein the tube is round.

9. The system of claim 1, wherein the sliding member is a solid bar.

10. The system of claim 1, comprising a plurality of railings, a plurality of sliding members for sliding along the railings and a connecting tube, wherein the connecting tube is rigidly connected to and substantially perpendicular to at least two of the sliding members.

11. The system of claim 10, where-in the connecting tube accommodates the actuating means.

* * * * *